(12) United States Patent
Schultink et al.

(10) Patent No.: US 7,582,142 B2
(45) Date of Patent: Sep. 1, 2009

(54) ABSORBING AGENT, DUST COLLECTION CHAMBER AND METHOD FOR ADSORBING ODOURS

(75) Inventors: Jan Schultink, Overpelt (BE); Ralf Sauer, Overpelt (BE)

(73) Assignee: Eurofilters N.V., Overpelt (BE)

( * ) Notice: Subject to any disclaimer, the term of this patent is extended or adjusted under 35 U.S.C. 154(b) by 325 days.

(21) Appl. No.: 10/590,175

(22) PCT Filed: Feb. 7, 2005

(86) PCT No.: PCT/EP2005/001214

§ 371 (c)(1),
(2), (4) Date: May 21, 2007

(87) PCT Pub. No.: WO2005/082219

PCT Pub. Date: Sep. 9, 2005

(65) Prior Publication Data

US 2008/0017036 A1 Jan. 24, 2008

(30) Foreign Application Priority Data

Mar. 1, 2004 (DE) ............... 10 2004 009 956
Oct. 15, 2004 (EP) ................... 04024608

(51) Int. Cl.
*A47L 9/12* (2006.01)
*B01D 53/02* (2006.01)

(52) U.S. Cl. .............. 95/285; 96/134; 96/135; 96/153; 96/154; 55/524; 55/527

(58) Field of Classification Search ............ 95/90, 95/273, 285, 901–903; 96/134, 135, 153, 96/154; 55/524, 527, DIG. 3; 210/502.1
See application file for complete search history.

(56) References Cited

U.S. PATENT DOCUMENTS

| 5,461,751 | A | | 10/1995 | Sepke | |
|---|---|---|---|---|---|
| 5,662,728 | A | * | 9/1997 | Groeger | 96/153 |
| 5,807,424 | A | * | 9/1998 | de Ruiter et al. | 95/148 |
| 5,871,569 | A | * | 2/1999 | Oehler et al. | 96/153 |
| 6,010,550 | A | | 1/2000 | Song | |
| 6,165,519 | A | * | 12/2000 | Lehrer et al. | 426/77 |
| 6,391,429 | B1 | * | 5/2002 | Senkus et al. | 428/198 |
| 6,423,123 | B1 | * | 7/2002 | Rosenberg et al. | 96/154 |
| 6,514,306 | B1 | * | 2/2003 | Rohrbach et al. | 55/524 |
| 6,610,128 | B2 | * | 8/2003 | Kishkovich | 96/153 |
| 6,630,233 | B1 | | 10/2003 | Levandowski et al. | |
| 6,726,751 | B2 | * | 4/2004 | Bause et al. | 96/134 |
| 6,840,986 | B1 | * | 1/2005 | Koslow | 96/135 |
| 6,936,094 | B2 | * | 8/2005 | Minemura et al. | 96/154 |

FOREIGN PATENT DOCUMENTS

| CA | 9 57 214 | 11/1974 |
|---|---|---|
| DE | 2 164 262 | 10/1972 |
| DE | 2 134 587 | 1/1973 |
| DE | 42 04 553 | 8/1993 |
| DE | 93 17 809 | 5/1995 |
| DE | 195 13 658 | 10/1995 |
| DE | 196 50 749 | 10/1997 |
| EP | 0 688 231 | 9/1997 |
| EP | 0 960 645 | 8/2003 |
| EP | 1 415 699 | 5/2004 |
| EP | 1 426 090 | 6/2004 |
| EP | 1 199 969 | 9/2004 |
| EP | 0 893 963 | 5/2007 |
| GB | 1 377 277 | 12/1974 |
| GB | 2 288 749 | 11/1995 |
| JP | 61 271 013 | 1/1986 |
| WO | 94/21305 | 9/1994 |
| WO | 01/08543 | 2/2001 |
| WO | 2004/052500 | 6/2004 |

* cited by examiner

*Primary Examiner*—Frank M Lawrence
(74) *Attorney, Agent, or Firm*—Fay Kaplun & Marcin, LLP

(57) ABSTRACT

Described is an adsorbing agent for dust-collecting filters, especially for adsorbing odors. The adsorbing agent may include fibers, flakes and/or granulate as a supporting material onto which a powdery adsorption material is applied superficially.

64 Claims, 5 Drawing Sheets

Figure 3

| Test series | Adsorption material | | Adsorbing agent | | | | Efficiency (%) | |
|---|---|---|---|---|---|---|---|---|
| | Type | Trade name Manufacturer | Supporting material | Amount of adsorbing agent used in the dust collection chamber (g) | Coating (%) | Amount of adsorbing agent in the dust collection chamber (g) | with 275 g dust | with 550 g dust |
| X | bamboo active charcoal | BW-Pulver, Aqua Air Adsorbens | split fibres 5 mm | 2,5 | 12 | 0,30 | 72 | 76 |
| X | wood active charcoal | HP5-Pulver, Aqua Air Adsorbens | split fibres 5 mm | 5 | 5 | 0,25 | 66 | 79 |
| X | cocnut shell active charcoal | CP2-Pulver Aqua Air Adsorbens | split fibres 5 mm | 10 | 4 | 0,40 | 77 | 63 |
| XI | wood active charcoal | HP5-Pulver Aqua Air Adsorbens | split fibres 5 mm | 2,5 | 5 | 0,13 | 54 | 54 |
| IX | CBP | CBP Kunz | split fibres 5 mm | 10 | 3 | 0,30 | 69 | 63 |
| XII | Zeolite 7,8 ; modulus 300 | DAY Degussa | split fibres 5 mm | 3 | 10 | 0,30 | 78 | 78 |
| XII | Zeolite 7,6 x 6,4 ; modulus 200 | TZB 2014 TRICAT | split fibres 5 mm | 3 | 10 | 0,30 | 59 | 59 |
| XII | Zeolite 7,8 ; modulus 100 | DALY TRICAT | split fibres 5 mm | 3 | 10 | 0,30 | 53 | 46 |
| XIV | Zeolite 5,5 ; modulus 1000 | TZP 9024 TRICAT | split fibres 5 mm | 3 | 10 | 0,30 | 29 | 21 |
| XIV | SDVB, macroporous | XAD 1600 Rohm & Haas | split fibres 5 mm | 3 | 13 | 0,39 | 74 | 46 |
| XII | SDVB, macroporous | MN200 MR4638 Purolite | split fibres 5 mm | 3 | 10 | 0,30 | 70 | 73 |
| XIX | SDVB, macroporous | MN200 MR4638 Purolite | macroporous polymer XAD1600 Rohm & Haas | 1,7 | 70 | 1,7 | 77 | 84 |

US 7,582,142 B2

ABSORBING AGENT, DUST COLLECTION CHAMBER AND METHOD FOR ADSORBING ODOURS

FIELD OF INVENTION

The present invention relates to a new adsorbing agent, especially for absorbing odours. The adsorbing agent comprises a specific supporting material and an adsorption material. The present invention relates furthermore to a dust collection chamber in which the adsorbing agent is contained. Finally, the invention also relates to a method for adsorbing odours.

BACKGROUND INFORMATION

In the prior art various measures are already known which lead to a reduction of odours emanating from dust deposited in filters.

One solution consists in leading the air which is laden with odorous substances through a separate downstream filter. Packed bed filters but also filters made of supporting structures which are coated with carbon or other adsorbing agents are used for this purpose. Such a solution is described in GB 2 288 749.

In the prior art it has also become known that odours may be masked by introducing bodies which are impregnated with aromatic principles into the filter chamber. Used for this purpose are fibre structures which are impregnated with perfume and sheathed in a plastics material wrapper, natural substances such as orange pips or orange skins for example, plastics material pieces to which perfume or natural essential oils have been applied during the injection moulding process, but also inorganic supporting materials such as sand/carbonates which are impregnated with aromatic principles (WO 94/21305). In the document U.S. Pat. No. 5,461,751 A, granulates which are impregnated with antibacterial and/or fungicidal substances are described.

Finally it is also known from WO 01/08543 A1 that an adsorbing agent may be introduced in loose form into a dust-collecting filter. Mentioned as adsorbing agents here are active charcoal, which can be in the form of pieces or spheres or also fibres, as well as zeolites and porous polymers.

The solution according to WO 01/08543 already shows a satisfying reduction of the odorous substances in the expelled air from upright vacuum cleaners. However this solution also has a serious disadvantage. In respect of the even distribution of the adsorbing agent in the filter bag it is desirable to use a light adsorbing agent which is as fine as possible. This has furthermore the advantage that the inner surface of the adsorbing agent is available on numerous relatively short paths (access pores). With the high load of fine dust in a vacuum-cleaner filter bag, by which the access pores can easily become clogged, it is only possible thus to guarantee that the inner surface is used almost completely for adsorbing odours.

Very fine particles, however, do not remain as desired homogenously mixed with the dust inside the filter bag but penetrate through the innermost filter layers and are for the most part deposited in the filter bag wall. This increases the resistance of the filter bag in an undesired manner (increase in pressure loss) and the adsorbing agent is no longer available to bind the odours. Through the use of relatively coarse-grained adsorbing agents, this increase in pressure loss of the filter bag can be avoided. The desired even distribution of the adsorbing agent in the filter bag is, however, worsened by the higher weight of the particles. In addition, the access pores quickly become clogged and only a small fraction of the inner surface remains available for adsorbing odour.

SUMMARY OF INVENTION

The present invention relates to a novel adsorbing agent and a dust collection chamber with which an improved reduction of the odours of dust deposited in dust collection chambers is achieved and in which the adsorption material is used effectively.

According to the present invention the adsorbing agent comprise fibres, flakes and/or granulate as the supporting material to which a powdery adsorption material is applied. The applicant was able to demonstrate that when such an adsorbing agent is used e.g. in a dust collection chamber, only a fraction of the adsorption material has to be used by comparison with the prior art. With the adsorbing agent according to the present invention, simultaneously a significant reduction of odours from the dust deposited in dust collection chambers is achieved. This is obviously due to the fact that the adsorbing agent present in fibres and/or flakes, under the operating conditions e.g. of a dust-collecting filter, is whirled up in the dust-collecting filter and thus mixes homogenously with the dust.

The use of purely powdery adsorption material which has a comparable mean particle size as it is applied to the fibres/flakes is normally not possible since otherwise the filter material easily becomes clogged.

In the adsorbing agent according to the present invention, the adsorption material can be present in an amount of between 1 and 100 wt-% in dependence on the supporting material and/or the method of application. In the case of the combination of supporting material and granulate or spherical particles of macroporous polymers and adsorption material comprising macroporous polymers, up to 100 wt-% adsorption material can be applied depending on the electrostatic charge. In the other cases the adsorption material is applied in an amount of between 1 and 40 wt-%, preferably in an amount of 7 to 25 wt-%. The adsorption material in powder form can here be applied over the entire surface or just to regions of the surface of the supporting material.

From the point of view of the material, in principle all the powdery materials known from the prior art can be used as the adsorption material. Particularly suitable here are active charcoal based on rock, wood, bamboo or coconut shell charcoal, active charcoal which is impregnated acid or alkaline or with silver salts, functionalised carbon, hydrophobic zeolites and/or hydrophobic, macroporous polymers.

The applicant was able to demonstrate that, in addition to powdery activated charcoal, functionalised carbon in the form of an aromatic carbon skeleton with functional groups is particularly suitable. Such an adsorbing agent has become known under the designation Carbonised Basal Plates (CBP). A description of these materials can be found at R. Kunz, 1816 North Cascade Avenue, Colorado Springs. The structure of such an adsorbing agent is reproduced in FIG. 1. This adsorbing agent has proved to be particularly suitable. Pulverised bamboo active charcoal has also proved suitable. Such an adsorbing material can be obtained e.g. from Aqua Air Adsorbens in DE-04509 Krostitz, Germany, under the designation BW 200.

It is preferred for the active charcoal to be used in a mean particle size of between 1 and 100, preferably between 15 and 50 µm.

It has become apparent that, in addition to the above-described active charcoal, selected zeolites are particularly suitable. Critical for suitability is firstly that the zeolite micropores are of an adequate size. Only above a diameter of 5 Å are the micropores in a position to absorb and bind typical odour molecules. In addition, the zeolite must have a strongly hydrophobic (non-polar) character. Only from a ratio of $SiO_2/Al_2O_3>200$ (modulus) is a zeolite sufficiently non-polar to bind the odour molecules. Particularly preferred are zeolites having a modulus>300. The surface exceeds 400 $m^2/g$. The particle size of the zeolites used was around 2 to 30 µm. The total pore volume is more than 0.2 $cm^2/g$ but agglomerates of these particles can also be used. In this case a higher total pore volume can be realised by the macropores produced. Such zeolites are accessible for example by de-aluminising types Y, 13C, ZSM5 and Beta.

In addition to zeolites, bentonites are also suitable, especially "Fuller's Earth".

The commercial types DAY (Degussa) and TZB 9013 (Tricat) and DALY (Tricat) have proved to be particularly suitable zeolites.

As a third particularly advantageous group must be mentioned macroporous (macroreticular) polymers. A typical representative is cross-linked SDVB (styrene-divinyl benzene). It is produced by copolymerisation of styrene with divinyl benzene in the presence of so-called porogens (pore-forming agents). Hydrophobic variants are used by preference which have a surface of >600 $m^2/g$ and micropores of 6 to 20 Å and as high a proportion as possible of mesopores (20 to 500 Å) and micropores (>500 Å). The average pore diameter is between 3 and 300 Å.

The particle size is advantageously between 1 and 500 µm. Particles of 1 to 200 µm are preferred. The pore volume of such products is typically >0.4 $cm^3/g$. Such macroporous polymers can be obtained commercially from Rohm & Haas (Amberlite), Purolite (Makronet), Dow Chemicals (Optipore), Mitsubishi Chemical Company (Sepabeads) and Bayer (I-ONAC).

A coating with porous crystalline organometallic complexes such as "MOF-177" for example is also suitable. This adsorbing agent realises an extremely large surface (4500 $m^2/g$) with sufficiently large micropores (10 Å). These crystals are described in Nature, Vol. 427, pages 523 to 527, February 2004. The disclosed content of this document is hereby incorporated by reference.

Fibres, flakes and/or granulate are proposed as supporting material for the adsorbing agent according to the present invention.

With respect to material, chemical fibres and/or natural fibres can be used as the fibres for the supporting material of the adsorbing agent. As chemical fibres, cellulose fibres such as viscose or synthetic fibres should be mentioned. Examples of synthetic fibres are fibres formed from polyolefins, polyester, polyamides, polyacryl methyl and/or polyvinyl alcohol.

Examples of natural fibres are cellulose, wood fibre materials, kapok, flax, jute, Manila hemp, coco, wood, cotton, Kenaf, abaca, mulberry bast and/or fluff pulp.

It has furthermore emerged that it is preferred for the fibres to be branched, crimped, hollow and/or textured and/or to have a non-circular (e.g. trilobal) cross-section.

As far as the dimensions are concerned, it is advantageous if the fibres have a mean length of between 0.3 mm and 100 mm, preferably between 0.5 and 70 mm.

The synthetic fibres can also be rendered antibacterial. This can come about in that antibacterial substances are added during the manufacturing process. The advantage of these fibres consists in the fact that the antibacterial substances are in practice not released and no reduction of the antibacterial effect occurs. Such fibres can be obtained from Rhovyl in F-55310 Tronville en Barrois, France, e.g. the fibres Rhovyl'A.S.® or from Japan Exlan Co. Ltd., Tokyo, as well as from Sterling Fibers Inc., 5005 Sterling Way, Pace, Fla. under the trade name "biofresh" and DAK Americas, 5925 Carnegie Blvd. Charlotte, N.C. 28209.

Naturally it is also possible to render the fibres antibacterial in a subsequent process.

According to the present invention, provision is also made for not only fibres to be used as the supporting material but also flakes. As suitable materials should be mentioned here foamed materials, non-woven materials, textiles, foamed starch, foamed polyolefins as well as films.

In the case of the flakes, diameters of 0.3 to 30 mm, preferably 0.5 to 20 mm, are advantageous. Particularly advantageous is a diameter of 1 to 9.5 mm.

According to the present invention, a granulate can also be used as the supporting material. Spherical particles are also understood as granulate in the sense of the present invention. Such spherical particles of polymers are referred to in this technology as "beads". According to a preferred variant, in particular macroporous synthetic polymers are used here as granulates/beads. The advantage of this variant can be seen in the fact that the adsorbing agent firstly as a supporting material comprises an adsorbing agent, namely macroporous polymers, to which then a second adsorbent material in powder form is applied. For the adsorbent material, all the adsorbent materials as described above can be used. Of macroporous polymers which are used as supporting material, those having a particle size of 0.2 to 1.5 mm, preferably of 0.3 to 1 mm, are preferred. The macroporous polymers as the supporting material can comprise polymers as already described above for the adsorption materials; by preference these macroporous synthetic polymers are constructed from polystyrene, acrylic acid and/or their derivatives. The specific surface is above 300 $m^2/g$, preferably in ranges between 400 and 1200 $m^2/g$. A further characteristic of porous polymers as the supporting material is that they have a pore volume which is greater than 0.4 ml/ml.

Such supporting materials can be obtained commercially e.g. from the firm Rohm & Haas and are marketed under the trade name Amberlite XAD. A further supplier is the company Purolite, which also offers suitable polymers under the trade name Makronet MN.

The adsorbing agent according to the present invention is so constructed that, on the supporting material as described above, the powdery adsorption material is applied chemically and/or physically to the surface of the supporting material.

Application in the sense of the present invention can be such that heated adsorption material is applied to the surfaces of the supporting material, so that melting occurs as a result of heat transfer to the surface of the supporting material and the powdery particles adhere. On the other hand, the surface of the supporting material can also be softened and then the particles applied to its surface. In the case of bi-component fibres, it is possible for the outer layer to have a lower melting point than the core, such that adherence of the particles is possible by heating said core.

Physically the application can take place by electrostatically charged supporting material being used. The procedure can take place with supporting material which is charged triboelectrically or by means of corona charge. Preferably charged split fibres are used for example. It is also possible to achieve the adhesion of the adsorption material to the supporting material by mixing suitable fibres, flakes, granulates and/or beads and adsorption material, the supporting material and the adsorption particles being then oppositely charged by the triboelectric effect. In this way an excellent electrostatic bond of the adsorbing agent particles to the supporting material is achieved without reducing the surface of the adsorbing agent particles by bonding agent. This possibility can be used particularly advantageously with the variant in which synthetic fibres are used with macroporous polymers. Thus for example the combination of polypropylene fibres with SDVB (styrene-divinyl benzene) powder exhibits a strong triboelectric charge on mixing. Surprisingly it has emerged that in the combination of a macroporous SDVB as the supporting material with an adsorption material based on macroporous SDVB functionalised with amine, a very defined triboelectric effect occurs which leads to a particularly secure bonding of the adsorption material to the supporting material.

The adsorbing agent as described above can also be present in an air-permeable wrapper. The advantage of this embodiment can be seen in the fact that the adsorbing agent is easy to handle and, when it is used for example in a dust-collecting filter in a vacuum cleaner, can be introduced into the dust-collecting filter without any problem. The wrapper for such an application is so constructed that it is destroyed again under the operating conditions such that the adsorbing agent can be whirled up in the dust-collecting filter and kept in circulation. Suitable materials for this purpose are non-wovens, e.g. non-woven with a low grammage, e.g. meltblown at 5 gr/m$^2$.

The present invention relates furthermore to a dust collection chamber. The dust collection chamber according to the present invention is characterised in that an adsorbing agent as described above is contained in it. It has proved to be advantageous for 0.03 to 5 g of the adsorbing agent to be contained in the dust collection chamber per 1000 cm$^3$ volume. By particular preference the amount of adsorbing agent is 0.3 to 2 g per 1000 cm$^3$. In the embodiment where powdery adsorption material is applied to granulate in the form of macroporous polymers, amounts of 0.05 to 1 g/1000 ml are sufficient. The dust collection chamber as described above is preferably in a so-called bagless vacuum cleaner, such as a cyclone vacuum cleaner for example.

For cyclone vacuum cleaners it is advantageous if porous polymers are used as the adsorption materials, since this causes no additional pollution due to carbon abrasion or the proportion of undersized material, and scratching of the generally transparent receptacles is avoided. According to the present invention, a refuse receptacle, e.g. a refuse bag, is also understood to be a "dust collection chamber".

According to the present invention, the term "dust collection chamber" refers in particular also to one which is formed by a dust-collecting filter made of an air-permeable filter material. In order to achieve the optimum effect of the adsorbing agent in the dust-collecting filter, it is preferable for this to be introduced in a loose form into the dust-collecting filter at the outset, or for the adsorbing agent to be present in the dust-collecting filter in a bag which has an air-permeable wrapper. The bag can then be fixed at one point e.g. directly in the impact area of the flow. The adsorbing agent can also lie in loose form in a part of the inner surface of the bag and be covered by a thin air-permeable non-woven layer (bag). This area can also be configured as a continuous strip. The adsorbing agent can also be present in a pad. A pad is used here which comprises at least one layer of a filter paper or of a special non-woven material on which the adsorbing agent lies. The adsorbing agent is then covered with at least one layer of a non-woven. This non-woven is so designed that it is destroyed under the operating conditions. Naturally the pad must be so arranged that the filter paper/the special non-woven is attached directly to the inside of the filter bag and the light non-woven is directly hit by the air flow. A particularly preferred embodiment of the air-permeable wrapper is a pad which is formed from a layer of filter paper having an air permeability >250 l/m$^2$/s, a filling with the adsorbing agent according to the present invention and a layer of a non-woven with a basis weight <10 g/m$^2$. This pad is then fixed in the dust collection chamber, for example by being glued at certain points, in such a way that the paper layer of the pad faces the filter material of the dust collection chamber. In this connection, the disclosed content of WO 2004/052500 A1, EP 1 426 090 A1 and EP 1 415 699 B1 is mentioned.

Such dust-collecting filters are preferably vacuum-cleaner bags. These are then usually of such dimensions and design that a volume flow rate of 10 m$^3$/h to 400 m$^3$/h is possible through them. It is preferred here for 0.3 to 5 g of the adsorbing agent to be contained in the dust-collecting filter per 1000 cm$^3$ volume, by particular preference 0.3 to 2 g adsorbing agent. When smaller amounts were used it was noted that no adequate odour-reducing effect is achieved and if larger amounts are used it is disadvantageous that the dust collection chamber as such is then already filled with too great a volume of adsorbing agent.

In terms of material, the dust-collecting filter according to the present invention here preferably comprises a filter material which can be a single layer or multi-layer paper and/or non-woven material. Such filter materials are known e.g. for vacuum-cleaner bags. Reference is made in this connection to EP-A 0 960 645 A1. The dust-collecting filter according to the present invention can be for example a vacuum-cleaner bag or also a pleated filter or a bag filter.

Finally, the present invention relates to a method for adsorbing odours in a dust collection.

The method according to the present invention for adsorbing odours is characterised in that an adsorbing agent as described above is used. By preference, 0.3 to 5 g adsorbing agent per 1000 cm$^3$ are used in the dust collection chamber.

For the method according to the present invention, a dust-collecting filter made of air-permeable filter material is used by preference as the dust collection chamber. For the method it is important that the adsorbing agent is present loose in the dust-collecting filter during the operation of said filter. The dust-collecting filter is here preferably a vacuum-cleaner bag. The adsorbing agent is thus either introduced into the dust-collecting filter during the manufacturing process or shortly thereafter and supplied in this way. When it is first used at a given volume flow rate there is then whirling-up of the adsorbing agent in the sealed dust-collecting filter and the adsorbing agent can develop its odour-reducing effect as described above. Naturally it is also possible for the adsorbing agent to be introduced at the start of the suction process, namely by the adsorbing agent being sucked up.

Furthermore, the adsorbing agent can be present in a wrapper and, again as described above, be already contained from the outset in the vacuum-cleaner bag or, however, the adsorbing agent is introduced with the wrapper into the vacuum-cleaner bag at the start of the suction process or it is sucked up directly.

For the method according to the invention it is particularly advantageous that the adsorbing agent can also be introduced subsequently i.e. directly at the start of the suction process, since in this way all previously popular filter bags can also be improved in their odour-reducing effect simply by sucking in or introducing the adsorbing agent before the first suction process. Naturally, if necessary, subsequent dosing can also take place. By particular preference, the method according to the invention is a method for vacuum cleaning using a cylinder vacuum cleaner or an upright vacuum cleaner and the dust-collecting filter is a vacuum-cleaner bag.

BRIEF DESCRIPTION OF DRAWINGS

The present invention is explained in greater detail below with the aid of an example and FIGS. 1 to 4.

FIG. 3 shows a summary in table form.

DETAILED DESCRIPTION

EXAMPLE

Figure 1:
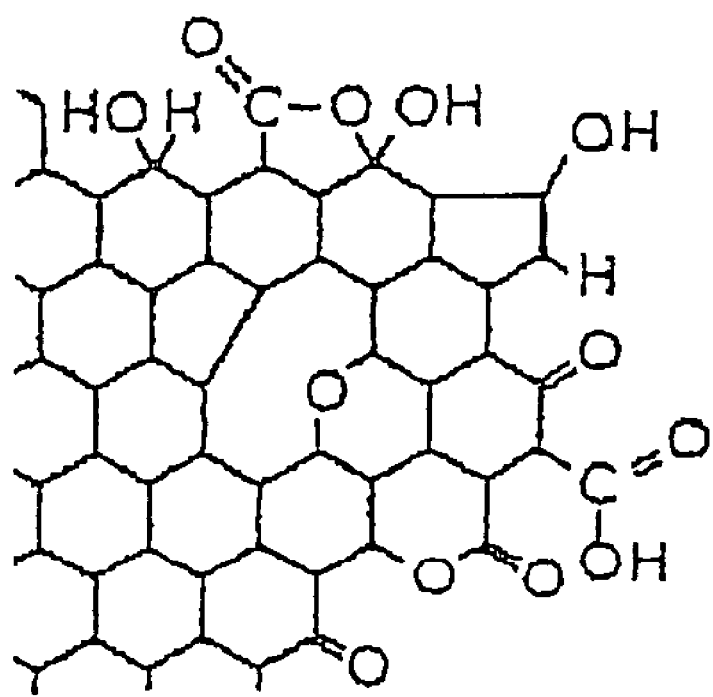
FIG. 1 shows a structure of functionalised carbon before it is used by preference as the adsorbing agent.

The tests which were carried out are described below with the aid of examples.

1) Preparation for Measurement:

The cylinder vacuum cleaners, type Miele S512-1 were operated with an empty filter bag for several hours before the series of measurements in order to minimise any odour already present in the assembly. One day before the actual start of measuring, a filter bag was inserted into each of the assemblies. Thereafter each assembly was completely sealed off so as to prevent the outgoing air escaping through any other aperture than the drilled sampling aperture (diameter 13 mm). Thereafter the assemblies were placed in the hot cabinet which was set at 20° C. Furthermore, the necessary amount of coffee for the entire series of measurements was removed from a 500 g vacuum pack, weighed and sealed in 5 g portions.

2) Sequence of Tests:

The test surface for sucking up the coffee/dust mixture comprises a sheet of laminate with a basal surface of 1.21 m×1.85 m, corresponding to 2.24 m². The cylinder vacuum cleaners were operated at the brush setting "carpet". To examine the reduction of odour in the vacuum-cleaner bag, for each assembly on test days 1 to 6, 50 g of test dust type 8 (DMT, composition: 70% mineral dust, 20% arbocell, 10% linters) as well as 5 g coffee (10% coffee relative to the amount of dust) were evenly distributed on the test surface. On the seventh and eighth test day, respectively 100 g dust and 10 g coffee were distributed and on the last test day only samples were taken. After the distribution of the coffee/dust mixture, the suction foot was placed on a clean piece of the test surface and, at a low suction power (300 watt), a sample bag having a total length of 1.5 m (filling amount approx. 15 litres) was filled directly from the sampling aperture of the sealed cylinder vacuum cleaner. After the sample bag had been removed (once completely full) and the assembly switched off, the sealing was completely removed and the suction power was adjusted up to maximum power (1600 watts). Then over a period of two minutes the coffee/dust mixture was vacuumed from the test surface. After sampling, the assemblies were switched off, again completely sealed and stored in the hot cabinet until the next sampling. On each test day, the temperature and the air humidity on removal from the hot cabinet as well as during sampling were measured.

3) Examined Variants and Equipment of the Assemblies

All the assemblies were operated with motor protection filters.

Variant A
Assembly A, 3 g split fibres/MN 200 MR 4636, loose in the filter bag,
Variant B
Assembly B, 3 g split fibres/DALY loose in the filter bag,
Variant C
Assembly C, 3 g split fibres/MN 200 MR 4638, loose in the filter bag,
Variant D
Assembly D, zero variant, empty filter bag,
Variant E
Assembly E, 3 g split fibres/TZB 2014 loose in the filter bag,
Variant F
Assembly F, 3 g split fibres/DAY loose in the filter bag.

4) Measuring and Analysis Methods 4.1 Odour Emissions 4.1.1 Measuring Method; Bases of the Method Determination of the odorous substance concentration in accordance with European standard DIN EN 13725.

4.1.2 Sampling Material

The sample air is drawn into a foil bag during static sampling. As sample bags are used commercially available foil tubes which comprise odourless material (Nalophan NA©) which on the one hand is practically gas-tight and on the other hand absorbs practically no odorous substances.

4.1.3 Olfactometer

Olfactometry represents a controlled presentation of air laden with odorous substances as well as a detection of the feelings aroused in a human by same. With the olfactometer, a gas sample (odorous substance sample) is diluted with neutral air and offered as an olfactory sample to test personnel (samplers). A sampling team comprises four odour assessors as well as a test manager who is responsible for operating the olfactometer during a measurement process.

For the described measurements, a computer-controlled olfactometer TO9 with four assessor places and automatic evaluation was used. The measurements were carried out according to DIN EN 13725. The olfactometer was operated with compressed air via a group of filters with silica gel (dehumidification), active charcoal (deposition of odorous substance), a cotton filter and fibre-glass microfine filter (dust deposition). The measurements were carried out according to the yes/no method as per DIN EN 13725.

Amounts of odorous substance are measured in odour units (OU) an OU corresponding to the amount of an odorous substance or of a substance mixture which—distributed at 20° C. and 1013 hPa in 1 m³ neutral air—triggers a perception of odour for 50% of a sampling team as per the definition of the odour threshold. The concentration of odorous substance at the odour threshold is by definition 1 OU/m³.

In an analogy with sound, levels of odorous substance are defined in respect of the threshold concentration of 1 OU/m³. For example an odorous substance concentration of 100 OU/m³ corresponds to an odorous substance level of 20 dB.

4.1.4 Description of the Sampling Team

The olfactometric measurements were taken by a test manager and four assessors in accordance with DIN EN 13725.

4.1.5 Evaluation of the Samples

The olfactometric measurement of the samples took place at the most four hours after sampling.

4.1.6 Number of Measurement Series per Measurement Day

Twelve measurements of the concentration of odorous substance, with three series per measurement. Respectively two of the measurements of the odorous substance concentration with n-butanol.

4.1.7 Other Tests

In order to additionally safeguard the results, the samples were examined on all the measuring days for intensity and hedonics (direct evaluation from the test bag in accordance with VDI regulation 3882).

Here odours which differed from the typical coffee (dust odour) of the test series were characterised by the assessors.

During the test series, room temperature and humidity were detected during sampling on the measuring days as well as the temperature and humidity in the respective hot cabinet on removal of the assemblies.

Figure 2:
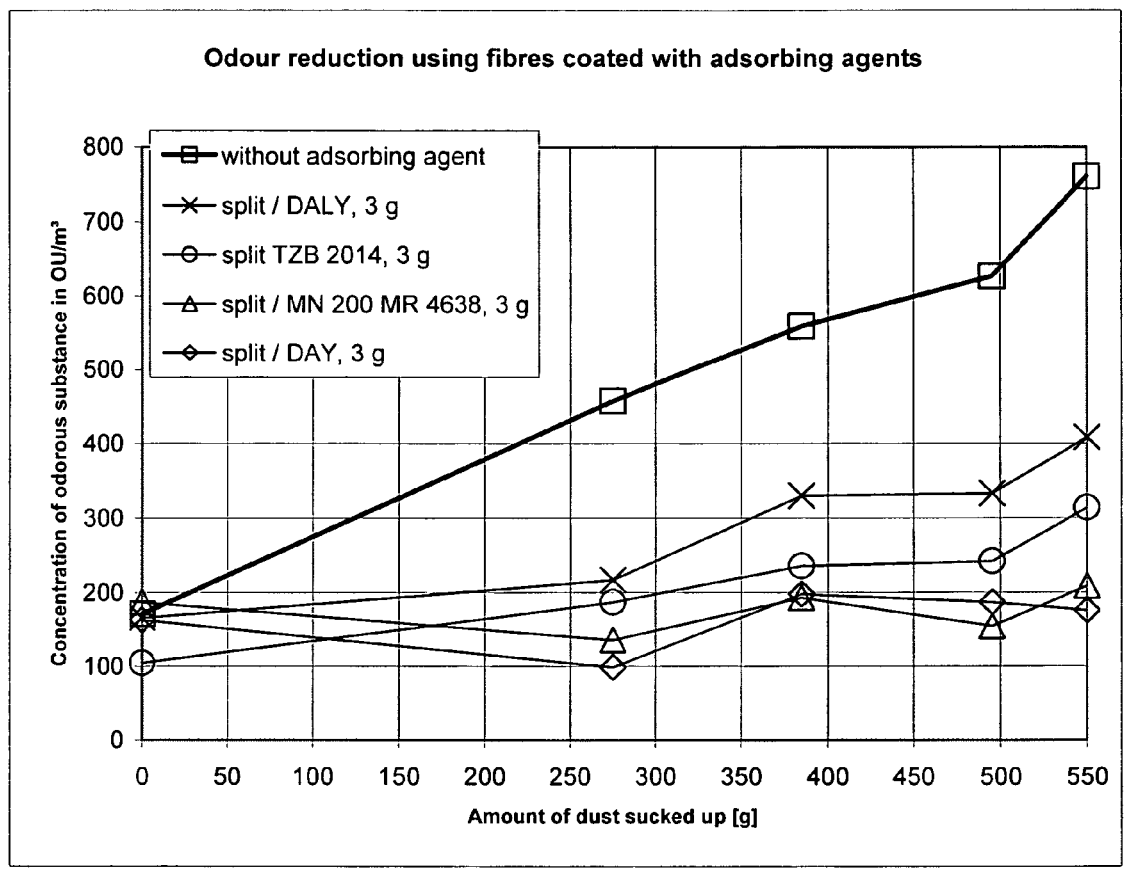
FIG. 2 shows in a graph the course of the concentration of odorous substance in the outgoing air in different samples.

FIG. 2 shows the pattern of the concentration of odorous substance in the outgoing air from vacuum cleaners of the five examined variants of the coated fibres in comparison with a zero variant. FIG. 2 makes it clear that all the examined variants cause a significant reduction in the concentration of odorous substance in the outgoing air. What is surprising here is particularly the good effect with the very small amount of adsorbing agent. Even with 0.3 g adsorbing agent, a significant reduction of the concentration of odorous substance can be achieved. The solutions which are currently usual, on the other hand, use 10 g active charcoal.

FIG. 3 shows the results summarised in table form.

In the summary in FIG. 3, in addition to the tests which are already contained in FIG. 2 and which are referred to as test series XII, there are also measurement results from additional tests.

The measurement results of test series X and XI relate here substantially to fibres coated with active charcoals. As is apparent from FIG. 3, the adsorbing agent according to the invention is characterised particularly in that even with the smallest amounts of adsorbing agent (e.g. 0.3 g bamboo active charcoal) already an above-average reduction of the concentration of odorous substance in the outgoing air is achieved.

Figure 4A:
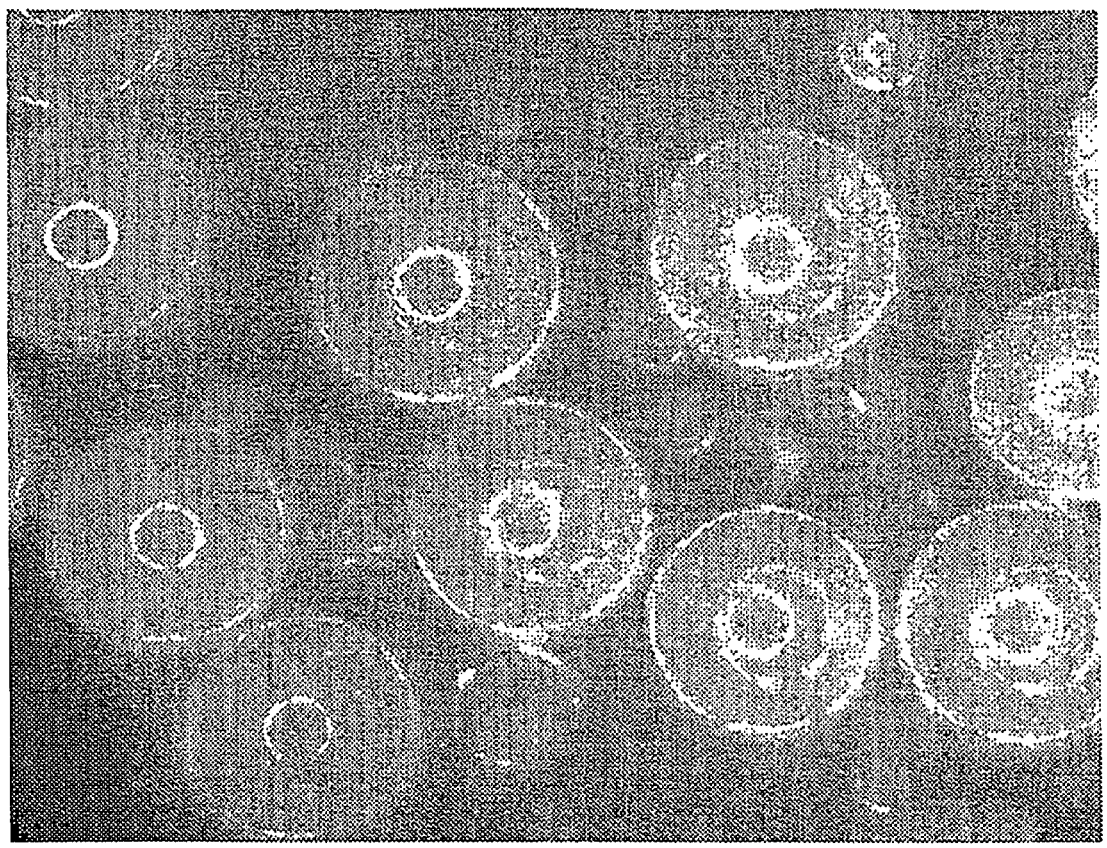
FIG. 4 shows an adsorbing agent according to the present invention in photographic view.
Figure 4B:
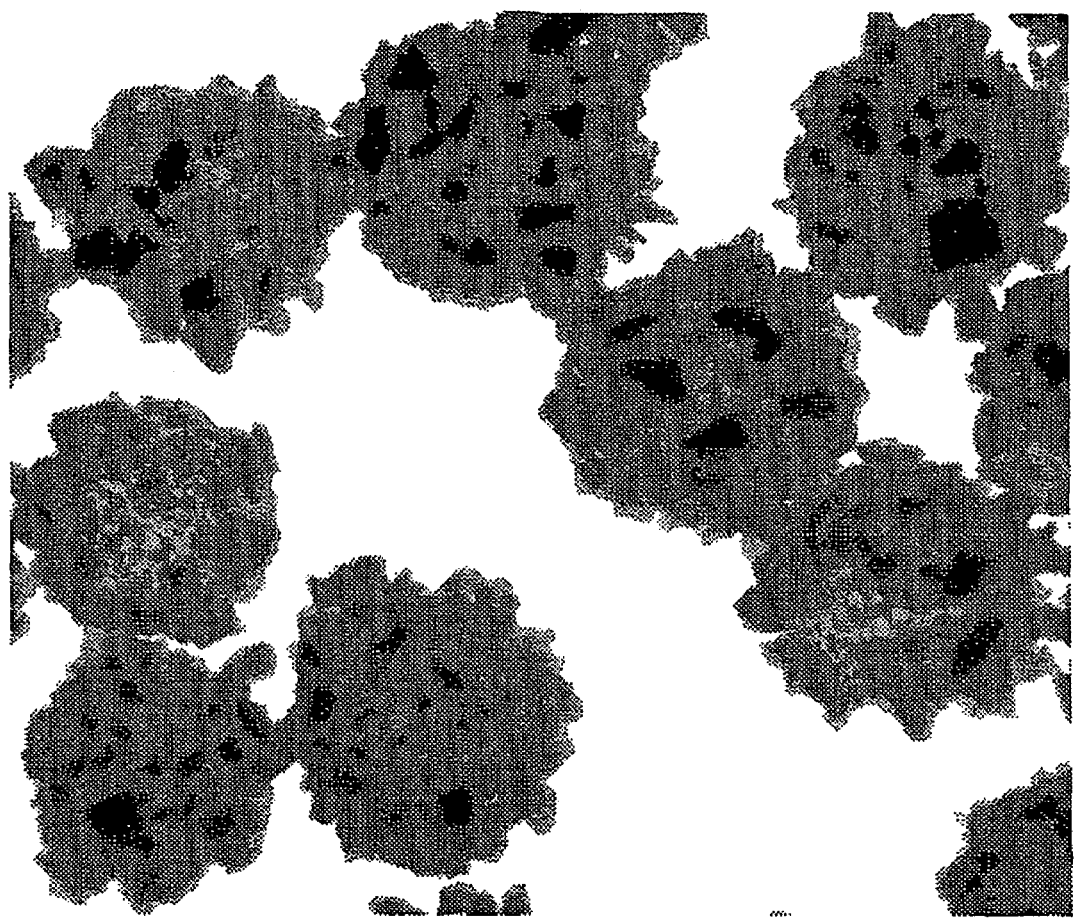

FIG. 4 shows an adsorbing agent according to the invention in the form of a photographic representation. The adsorbing agent which is illustrated in FIG. 4 comprises a macroporous supporting material (Rohm and Haas, XAD1600) which has been obtained from SDVB. The macroporous supporting material was used in the form of a so-called "bead" and has a particle diameter of 200-350 μm. The adsorption material which is applied to the macroporous polymer comprises macroporous polymers formed from functionalised SDVB (Purolite MN200). The adsorption material has a particle diameter of 0-40 μm. FIG. 4A shows uncoated beads of XAD1600 having a diameter of between 0.2 and 0.35 mm. FIG. 4B shows the XAD1600 beads according to the invention electrostatically coated with MN200 particles having a diameter of between 0 and 40 μm. As FIG. 4B shows, the macroporous adsorption material covers the supporting material almost completely. In the example according to FIG. 4B, 70 wt-% adsorption material relative to the supporting material was used.

The invention claimed is:

1. A dust-collecting filter, comprising:
   an air-permeable filter material; and
   an adsorbing agent being contained in a loose form in the dust-collecting filter, the adsorbing agent comprising at least one of fibres, flakes and granulate as a supporting material onto which a powdery adsorption material is applied superficially.

2. The dust-collecting filter according to claim 1, wherein the adsorption material is applied in an amount of between 1 and 50 wt-% of the supporting material.

3. The dust-collecting filter according to claim 2, wherein the adsorption material is applied in an amount of between 7 and 25 wt-% of the supporting material.

4. The dust-collecting filter according to claim 1, wherein the adsorption material is selected from at least one of active charcoal, impregnated active charcoal, functionalised carbon, hydrophobic zeolites, hydrophobic, porous polymers, bentonites and crystalline organometallic complexes.

5. The dust-collecting filter according to claim 4, wherein the functionalised carbon is an aromatic carbon skeleton with functional groups.

6. The dust-collecting filter according to claim 4, wherein the active charcoal is one of coconut shell, wood, rock and bamboo charcoal.

7. The dust-collecting filter according to claim 4, wherein the active charcoal is impregnated with at least one of (i) one of acid chemicals and basic chemicals an (ii) silver salts.

8. The dust-collecting filter according to claim 4, wherein the zeolites have micropores of a pore size >5 A.

9. The dust-collecting filter according to claim 8, wherein the pore size of the micropores is >6.5 A.

10. The dust-collecting filter according to claim 8, wherein a specific surface of the zeolites is >400 $m^2/g$.

11. The dust-collecting filter according to claim 8, wherein the zeolites have a modulus >200.

12. The dust-collecting filter according to claim 8, wherein the zeolites have a modulus >300.

13. The dust-collecting filter according to claim 8, wherein a particle size of the zeolites is in a range between 2 and 30 μm.

14. The dust-collecting filter according to claim 4, wherein the porous polymers have micropores of 6 to 20 A, mesopores of 20 to 500 A and macropores >500 A.

15. The dust-collecting filter according to claim 4, wherein an average pore diameter is between 3 and 300 A.

16. The dust-collecting filter according to claim 4, wherein a particle size of the porous polymers is in a range between 1 and 500 μm.

17. The dust-collecting filter according to claim 4, wherein a particle size of the porous polymers is in a range between 1 and 200 μm.

18. The dust-collecting filter according to claim 4, wherein a pore volume is equal to 0.4 $cm^3/g$.

19. The dust-collecting filter according to claim 4, wherein the porous polymers are constructed from at least one of styrene, acrylic acid and their derivatives.

20. The dust-collecting filter according to claim 1, wherein the adsorption material is at least one of chemically bound and physically bound to the supporting material.

21. The dust-collecting filter according to claim 1, wherein the adsorption material is bound to the supporting material which is electrostatically charged.

22. The dust-collecting filter according to claim 1, wherein the adsorption material is powdery and has a mean particle size between 1 and 100 μm.

23. The dust-collecting filter according to claim 1, wherein the supporting material comprises fibres which are selected from at least one of chemical fibres and natural fibres.

24. The dust-collecting filter according to claim 23, wherein the fibres are rendered antibacterial.

25. The dust-collecting filter according to claim 23, wherein the chemical fibres are cellulose fibres.

26. The dust-collecting filter according to claim 23, wherein the chemical fibres are at least one of viscose fibres and synthetic fibres.

27. The dust-collecting filter according to claim 26, wherein the synthetic fibres are selected from fibres formed from at least one of polyolefins, polyester, polyamides, polyacrylonitrile and polyvinyl alcohol.

28. The dust-collecting filter according to claim 23, wherein the natural fibres are selected from at least one of cellulose, wood fibre materials, kapok, flax, jute, Manila hemp, coco, wool, cotton, Kenaf, abaca, mulberry bast and fluff pulp.

29. The dust-collecting filter according to claim 23, wherein the fibres are at least one of smooth, branched, crimped, hollow and textured and have a non-circular cross-section.

30. The dust-collecting filter according to claim 23, wherein the fibres are at least one of smooth, branched, crimped, hollow and textured and have a trilobal cross-section.

31. The dust-collecting filter according to claim 23, wherein the fibres have a mean length of between 0.3 mm and 100 mm.

32. The dust-collecting filter according to claim 23, wherein the fibres have a mean length of between 0.5 mm and 70 mm.

33. The dust-collecting filter according to claim 23, wherein the fibres have a mean length of between 1 and 9.5 mm.

34. The dust-collecting filter according to claim 1, wherein the supporting material comprises flakes which are selected from cellular plastics, non-wovens, textiles, foamed starch, foamed polyolefins, as well as films and recovered fibres.

35. The dust-collecting filter according to claim 34, wherein the flakes have a diameter between 0.3 mm and 30 mm.

36. The dust-collecting filter according to claim 34, wherein the flakes have a diameter between 0.5 mm and 20 mm.

37. The dust-collecting filter according to claim 34, wherein the flakes have a diameter between 1 and 9.5 mm.

38. The dust-collecting filter according to claim 1, wherein the supporting material comprises granulates which are selected from macroporous polymers.

39. The dust-collecting filter according to claim 38, wherein a particle size of the granulates is in a range between 0.2 and 1.5 mm.

40. The dust-collecting filter according to claim 38, wherein a particle size of the granulates is in a range between 0.3 and 1.0 mm.

41. The dust-collecting filter according to claim 38, wherein the macroporous polymers are constructed from at least one of polystyrene, acrylic acid and their derivatives.

42. The dust-collecting filter according to claim 38, wherein a surface of the macroporous polymers is >200 m$^2$/g.

43. The dust-collecting filter according to claim 38, wherein a surface of the macroporous polymers is >350 m$^2$/g.

44. The dust-collecting filter according to claim 38, wherein a porosity is less or equal to 0.4 ml/ml.

45. The dust-collecting filter according to claim 1, wherein the adsorbing agent is enclosed in an air-permeable wrapper.

46. The dust-collecting filter according to claim 45, wherein the wrapper is an air-permeable non-woven.

47. The dust-collecting filter according to claim 1, wherein between 0.03 and 5 g of the adsorbing agent per 1000 cm$^3$ are contained in the dust-collecting filter.

48. The dust-collecting filter according to claim 47, wherein between 0.3 and 2 g of the adsorbing agent are contained per 1000 cm$^3$.

49. The dust-collecting filter according to claim 1, wherein the adsorbing agent is present in a bag, which has an air-permeable wrapper, in the dust-collecting filter.

50. The dust-collecting filter according to claim 49, wherein the adsorbing agent is arranged under a covering in part of an inner surface of the dust-collecting filter.

51. The dust-collecting filter according to claim 50, wherein the covering is a non-woven layer.

52. The dust-collecting filter according to claim 50, wherein the adsorbing agent is contained in a pad which is arranged on part of the inner surface of the dust-collecting filter.

53. The dust-collecting filter according to claim 52, wherein the pad comprises at least one layer of one of a filter paper and a special non-woven, the adsorbing agent arranged on the surface of the filter paper being covered by the at least one non-woven layer.

54. The dust-collecting filter according to claim 49, wherein the wrapper material of one of the bag and a covering is formed from a material which is destructible under operating conditions.

55. The dust-collecting filter according to claim 1, wherein the dust-collecting filter has predetermined dimensions and design to operate with a volume flow rate between 10 cm$^3$/h and 400 m$^3$/h.

56. The dust-collecting filter according to claim 1, wherein the filter material of the dust-collecting filter is at least one of (i) one of a single-layer paper and a multilayer paper and (ii) a non-woven material.

57. The dust-collecting filter according to claim 1, wherein the dust-collecting filter is a vacuum-cleaner bag.

58. The dust-collecting filter according to claim 1, wherein dust-collecting filter is one of a pleated filter and a bag filter.

59. A method, comprising:
adsorbing odours with a dust-collecting filter according to claim 1.

60. The method according to claim 59, wherein between 0.2 and 5 g of the adsorbing agent are used per 1000 cm$^3$ of the dust-collecting filter.

61. The method according to claim 59, further comprising:
introducing the adsorbing agent into the dust-collecting filter one of (i) before a start of a first suction process and (ii) at the start of the suction process.

62. The method according to claim 59, wherein the adsorbing agent is present in a wrapper and, the method further comprising:
introducing the adsorbing agent into the dust-collecting filter one of (i) before a start of a first suction process and (ii) at the start of the suction process.

63. The method according to claim 62, wherein the wrapper is destroyable at a predefined volume flow rate.

64. The method according to claim 59, wherein the method is for vacuum-cleaning using one of a cylinder vacuum-cleaner and an upright vacuum-cleaner.

* * * * *